(12) United States Patent
Tan et al.

(10) Patent No.: US 8,710,208 B2
(45) Date of Patent: Apr. 29, 2014

(54) METHOD TO QUANTIFY SIRNAS, MIRNAS AND POLYMORPHIC MIRNAS

(75) Inventors: Ruoying Tan, Palo Alto, CA (US); Caifu Chen, Palo Alto, CA (US); Karl J. Guegler, Menlo Park, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 13/456,835

(22) Filed: Apr. 26, 2012

(65) Prior Publication Data

US 2012/0301876 A1 Nov. 29, 2012

Related U.S. Application Data

(60) Division of application No. 13/015,332, filed on Jan. 27, 2011, now Pat. No. 8,187,815, which is a continuation of application No. 11/467,125, filed on Aug. 24, 2006, now abandoned.

(60) Provisional application No. 60/711,480, filed on Aug. 24, 2005, provisional application No. 60/750,302, filed on Dec. 13, 2005, provisional application No. 60/783,311, filed on Mar. 16, 2006.

(51) Int. Cl.
*C07H 21/04* (2006.01)
*C12Q 1/68* (2006.01)

(52) U.S. Cl.
USPC .................. 536/24.3; 536/24.2; 435/6.12

(58) Field of Classification Search
None
See application file for complete search history.

(56) References Cited

U.S. PATENT DOCUMENTS

| | | | |
|---|---|---|---|
| 6,027,923 A | 2/2000 | Wallace | |
| 6,030,788 A | 2/2000 | Gerhold | |
| 6,117,635 A | 9/2000 | Nazarenko et al. | |
| 6,406,891 B1 | 6/2002 | Legerski et al. | |
| 6,548,250 B1 | 4/2003 | Sorge et al. | |
| 6,777,180 B1 * | 8/2004 | Fisher et al. | 435/6.16 |
| 2003/0050444 A1 | 3/2003 | Haydock et al. | |
| 2004/0014058 A1 | 1/2004 | Alsobrook et al. | |
| 2004/0203061 A1 | 10/2004 | Barany et al. | |
| 2005/0074788 A1 | 4/2005 | Dahlberg et al. | |

(Continued)

FOREIGN PATENT DOCUMENTS

| | | |
|---|---|---|
| EP | 1138764 | 10/2001 |
| WO | WO-01/94634 | 12/2001 |
| WO | WO-2005/094532 | 10/2005 |

OTHER PUBLICATIONS

Chen, C. et al., "Real-time quantification of microRNAs by stem-loop RT-PCR", *Nucleic Acids Research. Oxford University Press. Surrey. GB.* vol. 33. No. 20., XP002420559,ISSN: 0305-1048, Jan. 1, 2005, 1-9.

(Continued)

*Primary Examiner* — Samuel Woolwine

(57) ABSTRACT

The present teachings provide methods, compositions, and kits for quantifying target polynucleotides. In some embodiments, a reverse stem-loop ligation probe is ligated to the 3' end of a target polynucleotide, using a ligase that can ligate the 3' end of RNA to the 5' end of DNA using a DNA template, such as T4 DNA ligase. Following digestion to form an elongated target polynucleotide with a liberated end, a reverse transcription reaction can be performed, followed by a PCR. In some embodiments, the methods of the present teachings can discriminate between polymorphic polynucleotides that vary by as little as one nucleotide.

18 Claims, 2 Drawing Sheets

(56) References Cited

U.S. PATENT DOCUMENTS

| | | | |
|---|---|---|---|
| 2005/0255487 A1* | 11/2005 | Khvorova et al. | 435/6 |
| 2005/0266418 A1* | 12/2005 | Chen et al. | 435/6 |
| 2005/0272075 A1 | 12/2005 | Jacobsen et al. | |
| 2006/0057595 A1 | 3/2006 | Lao et al. | |

OTHER PUBLICATIONS

Chen, C. et al., "Real-time PCR: Advancing RNA Interference and MicroRNA Studies", 2005, 5 pages.

Eggerding, F. A. et al., "A One-Step Coupled Amplification and Oligonucleotide Ligation Procedure for Multiplex Genetic Typing", *PCR Methods & Applications,Cold Spring Harbor Laboratory Press, US,*, vol. 4, No. 6, 1995, 337-345.

Eldering, E. et al., "Expression profiling via novel multiplex assay allows rapid assessment of gene regulation in defined signalling pathways", *Nucleic Acids Research*, vol. 31, No. 23, pp. 1362-4962, Dec. 1, 2003, p. 153.

06802531.1, "European Supplementary Search Report dated Nov. 27, 2008", 5 Pgs.

06850497.6, "European Supplementary Search Report dated Dec. 1, 2008", 3 Pgs.

Liang, D-C et al., "Multiplex RT-PCR assay for the detection of major fusion transcripts in Taiwanese children with B-lineage acute lymphoblastic leukemia", *Medical and Pediatric Oncology*, vol. 39, No. 1,XP002506296; ISSN: 0098-1532, Jul. 2002, 12-17.

PCT/US2006/021172, "International Search Report dated Aug. 9, 2007", 1 Pg.

PCT/US2006/033642, "Search Report and Written Opinion dated Aug. 24, 2006", 12 Pgs.

Tse, W. T. et al., "Reverse Transcription and Direct Amplification of Cellular RNA Transcripts by TAQ Polymerase", *Gene. Elsevier, Amsterdam. NL,*XP000226751, vol. 88, No. 2,I SSN: 0378-1119, Apr. 16, 1990, 293-296.

* cited by examiner

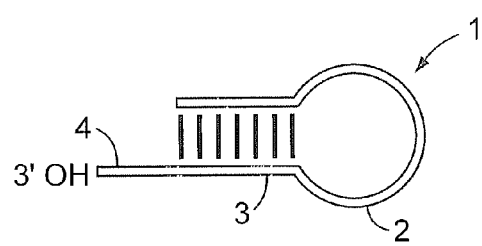
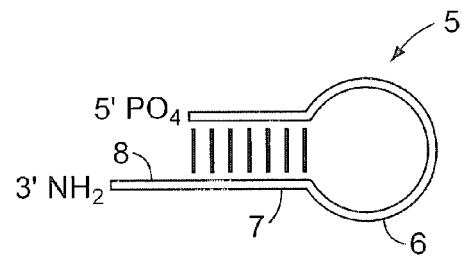
FIG. 1          FIG. 2
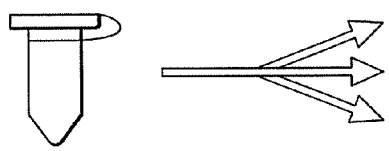
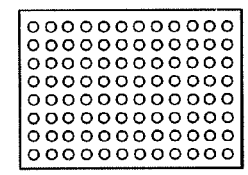
FIG. 3
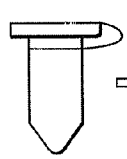
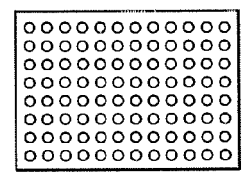
FIG. 4

```
                        SEQUENCE LISTING

<160> NUMBER OF SEQ ID NOS: 65

<210> SEQ ID NO 1
<211> LENGTH: 47
<212> TYPE: DNA
<213> ORGANISM: Artificial Sequence
<220> FEATURE:
<223> OTHER INFORMATION: Description of Combined DNA/RNA Molecule:
      Synthetic probe
<220> FEATURE:
<223> OTHER INFORMATION: Description of Artificial Sequence: Synthetic
      probe

<400> SEQUENCE: 1
gacgcaaagg aagagtggga gcgtgcuucu uccuuugcgt cgcggag              47

<210> SEQ ID NO 2
<211> LENGTH: 47
<212> TYPE: DNA
<213> ORGANISM: Artificial Sequence
<220> FEATURE:
<223> OTHER INFORMATION: Description of Combined DNA/RNA Molecule:
      Synthetic probe
<220> FEATURE:
<223> OTHER INFORMATION: Description of Artificial Sequence: Synthetic
      probe

<400> SEQUENCE: 2
ccaggcaaga agccgccaac ctctcguucc uucuugcctg gagcgga              47

<210> SEQ ID NO 3
<211> LENGTH: 47
<212> TYPE: DNA
<213> ORGANISM: Artificial Sequence
<220> FEATURE:
<223> OTHER INFORMATION: Description of Combined DNA/RNA Molecule:
      Synthetic probe
<220> FEATURE:
<223> OTHER INFORMATION: Description of Artificial Sequence: Synthetic
      probe

<400> SEQUENCE: 3
gaggcaagga agtggcggta gctggcuuac uuccuugcct caagcgg              47

<210> SEQ ID NO 4
<211> LENGTH: 47
<212> TYPE: DNA
<213> ORGANISM: Artificial Sequence
<220> FEATURE:
<223> OTHER INFORMATION: Description of Combined DNA/RNA Molecule:
      Synthetic probe
<220> FEATURE:
<223> OTHER INFORMATION: Description of Artificial Sequence: Synthetic
      probe
```

-continued

```
<400> SEQUENCE: 4
gacaacgaga cacctgcgag tgacccuugu gucucgutgt caaagcg         47

<210> SEQ ID NO 5
<211> LENGTH: 47
<212> TYPE: DNA
<213> ORGANISM: Artificial Sequence
<220> FEATURE:
<223> OTHER INFORMATION: Description of Combined DNA/RNA Molecule:
      Synthetic probe
<220> FEATURE:
<223> OTHER INFORMATION: Description of Artificial Sequence: Synthetic
      probe

<400> SEQUENCE: 5
gacggcaagg aggtccgcac tctccguucc uccuugccgt caaaagc         47

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgcgctcttc gtcgctg                                          17

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgcgctcttc gtcgctg                                          17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgcgctcttc gtcgctg                                          17

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgcgctcttc gtcgctg                                          17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 10
cgcgctcttc gtcgctg                                                17

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcacgctccc actcttc                                                17

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gagaggttgg cggct                                                  15

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cagctaccgc cacttc                                                 16

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gggtcactcg caggtg                                                 16

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gagagtgcgg acctcc                                                 16

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
```

-continued ctttgcgtcg cggaga                                                16

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
cttgcctgga gcggaga                                               17

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
ttgcctcaag cggagac                                               17

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
tcgttgtcaa agcggag                                               17

<210> SEQ ID NO 20
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
tgccgtcaaa agc                                                   13

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcacgctccc actcttc                                               17

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gagaggttgg cggctt                                                16

<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gccagctacc gccact                                                          16

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gggtcactcg caggtgt                                                         17

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cggagagtgc ggacctc                                                         17

<210> SEQ ID NO 26
<211> LENGTH: 51
<212> TYPE: DNA
<213> ORGANISM: Artificial Sequence
<220> FEATURE:
<223> OTHER INFORMATION: Description of Combined DNA/RNA Molecule:
      Synthetic probe
<220> FEATURE:
<223> OTHER INFORMATION: Description of Artificial Sequence: Synthetic
      probe

<400> SEQUENCE: 26
gcactgatgg cagaccgatc cttggttgca uuucugccau cagugcacgc g                   51

<210> SEQ ID NO 27
<211> LENGTH: 51
<212> TYPE: DNA
<213> ORGANISM: Artificial Sequence
<220> FEATURE:
<223> OTHER INFORMATION: Description of Combined DNA/RNA Molecule:
      Synthetic probe
<220> FEATURE:
<223> OTHER INFORMATION: Description of Artificial Sequence: Synthetic
      probe

<400> SEQUENCE: 27
ttaccgacgt cagagcccag tctaatcgca uuucugacgu cgguaatacg c                   51

<210> SEQ ID NO 28
<211> LENGTH: 51
<212> TYPE: DNA
<213> ORGANISM: Artificial Sequence
<220> FEATURE:
<223> OTHER INFORMATION: Description of Combined DNA/RNA Molecule:
      Synthetic probe

```
<220> FEATURE:
<223> OTHER INFORMATION: Description of Artificial Sequence: Synthetic
      probe

<400> SEQUENCE: 28
ggacccatgt cagacctcac acactacctg uuucugacau ggguccctac g            51

<210> SEQ ID NO 29
<211> LENGTH: 51
<212> TYPE: DNA
<213> ORGANISM: Artificial Sequence
<220> FEATURE:
<223> OTHER INFORMATION: Description of Combined DNA/RNA Molecule:
      Synthetic probe
<220> FEATURE:
<223> OTHER INFORMATION: Description of Artificial Sequence: Synthetic
      probe

<400> SEQUENCE: 29
ggactgatcg cagagagcaa gcagttcact uuucugcgau caguccacta c            51

<210> SEQ ID NO 30
<211> LENGTH: 51
<212> TYPE: DNA
<213> ORGANISM: Artificial Sequence
<220> FEATURE:
<223> OTHER INFORMATION: Description of Combined DNA/RNA Molecule:
      Synthetic probe
<220> FEATURE:
<223> OTHER INFORMATION: Description of Artificial Sequence: Synthetic
      probe

<400> SEQUENCE: 30
gcagcgatct cagaggctcg tgatcatgaa uuucugagau cgcugcgact a            51

<210> SEQ ID NO 31
<211> LENGTH: 51
<212> TYPE: DNA
<213> ORGANISM: Artificial Sequence
<220> FEATURE:
<223> OTHER INFORMATION: Description of Combined DNA/RNA Molecule:
      Synthetic probe
<220> FEATURE:
<223> OTHER INFORMATION: Description of Artificial Sequence: Synthetic
      probe

<400> SEQUENCE: 31
ggactgatgg cagacggatc gttggttgct uuucugccau cagucccaag t            51

<210> SEQ ID NO 32
<211> LENGTH: 51
<212> TYPE: DNA
<213> ORGANISM: Artificial Sequence
<220> FEATURE:
<223> OTHER INFORMATION: Description of Combined DNA/RNA Molecule:
      Synthetic probe
<220> FEATURE:
<223> OTHER INFORMATION: Description of Artificial Sequence: Synthetic
      probe

<400> SEQUENCE: 32
ttacggacgt cagagcccag tctaatcgca uuucugacgu ccguaaacaa g            51

<210> SEQ ID NO 33
<211> LENGTH: 51
<212> TYPE: DNA
<213> ORGANISM: Artificial Sequence
<220> FEATURE:
<223> OTHER INFORMATION: Description of Combined DNA/RNA Molecule:
      Synthetic probe
```

```
<220> FEATURE:
<223> OTHER INFORMATION: Description of Artificial Sequence: Synthetic
      probe

<400> SEQUENCE: 33
ttaggcaggt cagacatcgt accctaccag uuucugaccu gccuaacaca a              51

<210> SEQ ID NO 34
<211> LENGTH: 51
<212> TYPE: DNA
<213> ORGANISM: Artificial Sequence
<220> FEATURE:
<223> OTHER INFORMATION: Description of Combined DNA/RNA Molecule:
      Synthetic probe
<220> FEATURE:
<223> OTHER INFORMATION: Description of Artificial Sequence: Synthetic
      probe

<400> SEQUENCE: 34
ggactgatcg cagagagcaa gcagtactct uuucugcgau cagucccac a               51

<210> SEQ ID NO 35
<211> LENGTH: 51
<212> TYPE: DNA
<213> ORGANISM: Artificial Sequence
<220> FEATURE:
<223> OTHER INFORMATION: Description of Combined DNA/RNA Molecule:
      Synthetic probe
<220> FEATURE:
<223> OTHER INFORMATION: Description of Artificial Sequence: Synthetic
      probe

<400> SEQUENCE: 35
gcagtgacct cagagggagc tgatcatgaa uuucugaggu cacugcacca c              51

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gctccgctat tgcttaagaa tacgc                                           25

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gctccgctat tgcttaagaa tacgc                                           25

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gctccgctat tgcttaagaa tacgc                                           25
```

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
gctccgctat tgcttaagaa tacgc         25

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
gctccgctat tgcttaagaa tacgc         25

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
gccgaacccg tagatccgaa         20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
gccgaacccg tagatccgaa         20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
gccgaacccg tagatccgaa         20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
gccgaacccg tagatccgaa         20

<210> SEQ ID NO 45
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gccgaacccg tagatccgaa                                                     20

<210> SEQ ID NO 46
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
tgccatcagt gcacg                                                          15

<210> SEQ ID NO 47
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
tgacgtcggt aatacg                                                         16

<210> SEQ ID NO 48
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
tgacatgggt ccctacg                                                        17

<210> SEQ ID NO 49
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
tgcgatcagt ccactac                                                        17

<210> SEQ ID NO 50
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
tgagatcgct gcgacta                                                        17

<210> SEQ ID NO 51
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 51
tgccatcagt cccaagt                                                17

<210> SEQ ID NO 52
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
tgacgtccgt aaacaa                                                 16

<210> SEQ ID NO 53
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
tgacctgcct aacacaa                                                17

<210> SEQ ID NO 54
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
tgcgatcagt ccccaca                                                17

<210> SEQ ID NO 55
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
tgaggtcact gcaccac                                                17

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tgcaaccaag gatcggtc                                               18

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
```

-continued

```
primer

<400> SEQUENCE: 57
tgcgattaga ctgggctc                                                 18

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
caggtagtgt gtgaggtc                                                 18

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
agtgaactgc ttgctctc                                                 18

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ttcatgatca cgagcctc                                                 18

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
agcaaccaac gatccgtc                                                 18

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tgcgattaga ctgggctc                                                 18

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 63
ctggtagggt acgatgtc                                                        18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
agagtactgc ttgctctc                                                        18

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ttcatgatca gctccctc                                                        18
```

METHOD TO QUANTIFY SIRNAS, MIRNAS AND POLYMORPHIC MIRNAS

CROSS-REFERENCE TO RELATED APPLICATIONS

This application is a divisional application of U.S. patent application Ser. No. 13/015,332 filed Jan. 27, 2011, now U.S. Pat. No. 8,187,815 B2, which is a continuation of U.S. patent application Ser. No. 11/467,125 filed Aug. 24, 2006, now abandoned, which claims a priority benefit under 35 U.S.C. §119(e) from U.S. Patent Application Ser. No. 60/711,480 filed Aug. 24, 2005, U.S. Patent Application Ser. No. 60/750, 302 filed Dec. 13, 2005, and U.S. Patent Application Ser. No. 60/783,311 filed Mar. 16, 2006, all of which are incorporated herein by reference in their entirety.

The present teachings relate to methods, compositions, and kits for amplifying, identifying, and quantitying polymorphic target polynucleotides.

INTRODUCTION

In 1998, Andrew Fire and Craig Mello discovered that injection of double-stranded RNA (dsRNA) into *Caenorhabditis elegans* could initiate a potent sequence-specific degradation of cytoplasmic mRNAs (Fire, et al., 1998, Nature, 391, 806-811). In mammalian cells, RNA interference (RNAi) can be triggered by a variety of dsRNA or dsRNA-domain-containing molecules that are processed by the endoribonuclease Drosha and Dicer. Dicer is also responsible for the processing of foreign dsRNA or dsRNA-domain-containing molecules into small duplex RNAs termed small interfering RNAs (siRNAs). One strand (anti sense strand) of the siRNA is incorporated into a ribonucleoprotein complex to form the RNA-induced silencing complex (RISC) that can mediate RNA silencing (Bartel, 2004 Cell (2004), 116, 281-297).

Two broad categories of RNA interferences (RNAi) effective molecules have been developed: (1) synthetic siRNA duplexes formed from two complementary but independent strands; and (2) vector-expressed short hairpin (sh)RNA that is processed into siRNA in vivo. The primary advantage in the use of synthetic siRNAs is the ability to control the amount of siRNA, which may minimize the possibility of nonspecific effects, but the key disadvantage of synthetic siRNA is the transient nature of the silencing effect. The key advantage of shRNA resides in the ability to express these transcripts from plasmid or viral-based expression vector continuously. Both synthetic dsRNAs and shRNAs have been widely used in investigation gene function and are being developed as therapeutic agents (Dykxhoorn, et al., 2003, Nature Review Molecular Cell Biology (2003), 4, 457-467, and Dorsett and Tuschl 2004, Nature Reviews Drug Discovery (2004), 3, 318-329.).

shRNAs driven by polymerase III promoters have been predominantly investigated as an alternative strategy to stably suppress gene expression (Zheng, et al., 2003, Proc. Natl. Acad. Sci. USA 101, 135-140; Shirane, et al., 2003, Nature Genet (2004), 36, 190-196; and Sen, et al., 2004, Nature Genet. 36, 183-189). Since the position at which Dicer RNase III cleaves a hairpin of shRNA is not well defined and transcriptional termination can be ambiguous, a shRNA expression may generate multiple siRNA species (see FIG. 1, Dorsett and Tuschl, 2004). Quantification of shRNA-derived siRNAs will provide useful information for the designing of shRNA constructs and for the development of shRNA-based RNAi therapeutics. Pre-miRNA may also be ambiguously processed by Dicer into multiple miRNA species (polymorphic miRMA) in vivo, identification of polymorphic miRNAs would provide insights for miRNA study.

Approaches to quantify miRNAs and other short target polynucleotides have been described in U.S. Non-Provisional application Ser. Nos. 10/947,460, and 11/142,720 to Chen et al.

SUMMARY

In some embodiments, the present teachings provide a method of amplifying a target polynucleotide, the method comprising; forming a first reaction complex comprising a reverse stem-loop ligation probe hybridized to the target polynucleotide, wherein the reverse stem-loop ligation probe comprises a loop, a stem, and a 3' target-specific portion; ligating the reverse stem-loop ligation probe to the target polynucleotide to form an elongated target polynucleotide; removing the hybridized 3' target-specific portion from the elongated target polynucleotide to form an elongated target polynucleotide with a liberated end; forming a second reaction complex comprising a reverse primer hybridized to the liberated end of the elongated target polynucleotide; extending the reverse primer to form a first strand, wherein the first strand is hybridized to the elongated target polynucleotide to form a double stranded complex; and, amplifying the double stranded complex.

In some embodiments, the present teachings provide a reaction composition comprising at least three species of reverse stem-loop ligation probes, wherein the at least three species of reverse stem-loop ligation probes vary from each other in the sequence of the 3' target-specific portion, wherein the at least three species of reverse stem-loop ligation probes vary from each other in the sequence of their stem, and wherein the at least three species reverse stem-loop ligation probes vary from each other in the sequence of their loop.

The present teachings provide additional methods, reaction compositions, and kits, some employing reverse stem-loop primers as well as reverse stem-loop ligation probes.

DRAWINGS

FIG. 1 depicts one reverse stem-loop primer in accordance with some embodiments of the present teachings.

FIG. 2 depicts one reverse stem-loop ligation probe in accordance with some embodiments of the present teachings.

FIG. 3 depicts one work-flow for performing a multiplexed reverse transcription reaction with a plurality of reverse stem-loop primers to query a plurality of polymorphic polynucleotides in accordance with some embodiments of the present teachings.

FIG. 4 depicts one work-flow for performing a multiplexed ligation reaction with a plurality of reverse stem-loop ligation probes to query a plurality of polymorphic polynucleotides in accordance with some embodiments of the present teachings.

DESCRIPTION OF EXEMPLARY EMBODIMENTS

Figure 5:
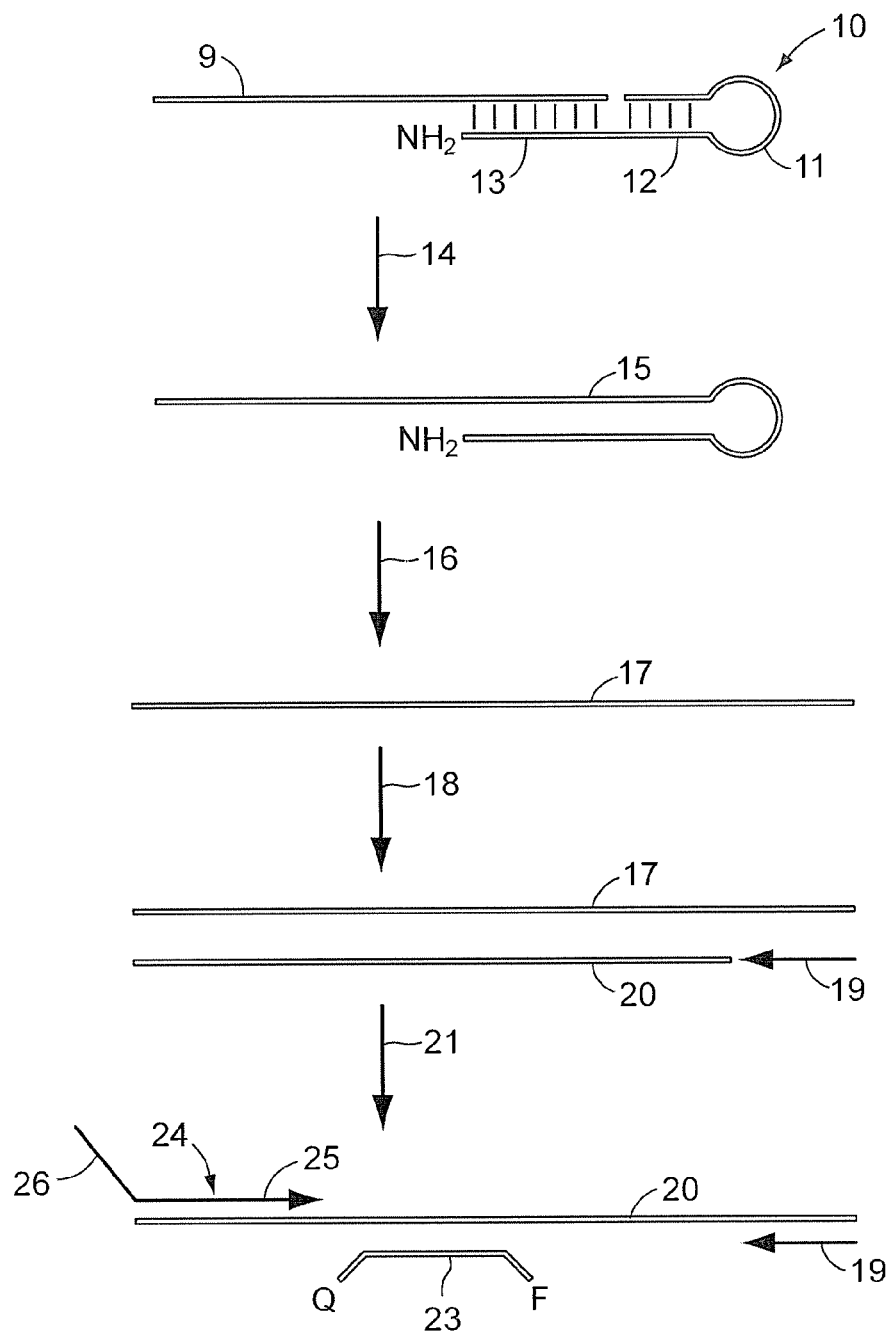
FIG. 5 depicts one reaction scheme for performing ligation reaction with a reverse stem-loop ligation probe to query a target polynucleotide in accordance with some embodiments of the present teachings.

It is to be understood that both the foregoing general description and the following detailed description are exemplary and explanatory only and are not intended to limit the scope of the current teachings. In this application, the use of the singular includes the plural unless specifically stated otherwise. Also, the use of "comprise", "contain", and "include", or modifications of those root words, for example but not limited to, "comprises", "contained", and "including", are not intended to be limiting. The term and/or means that the terms before and after can be taken together or separately. For illustration purposes, but not as a limitation, "X and/or Y" can mean "X" or "Y" or "X and Y".

The section headings used herein are for organizational purposes only and are not to be construed as limiting the described subject matter in any way. All literature and similar materials cited in this application, including, patents, patent applications, articles, books, treatises, and internet web pages are expressly incorporated by reference in their entirety for any purpose. In the event that one or more of the incorporated literature and similar defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

In some embodiments, the present teachings provide a novel ligation-based PCR assay for querying polymorphic polynucleotides, for example each species of shRNA-derived siRNAs. In some embodiments, we have applied the assays provided by the present teachings to discover and quantify polymorphic miRNAs whose 3' end is different from that of mature miRNA in Sanger's data base. One aspect of the complexity of nucleic acid biology inside a typical cell results from the observation that each shRNA expressed may generate multiple siRNA species. This can result from, for example, ambiguous transcription termination by poly III, and/or ambiguous cleavage by Dicer. Thus, a plurality of polymorphic polynucleotides arise from a single shRNA.

Thus, in one aspect the present teachings provide for novel RT primer and ligation probe designs that can selectively discriminate between a plurality of different polymorphic target polynucleotides. These target polynucleotides can differ only slightly in their 3' end, by as little as a single nucleotide. For example, FIG. 1 depicts a design for a reverse stem-loop primer according to some embodiments of the present teachings. Here, the reverse stem-loop primer (1) comprises a 3' target-specific portion (4), a stem (3), and a loop (2). The 3' end of the reverse stem-loop primer is shown containing a free 3'OH group, thus allowing its extension by an enzyme such as a polymerase, reverse transcriptase, etc.

In some embodiments, for example when a plurality of different polymorphic polynucleotides are to be queried in a single sample, the different regions of the reverse stem-loop primer can be encoded as follows: The 3' target-specific portion is complementary to a particular polymorphic target polynucleotide; the stem encodes a detector probe binding site, or complement to a detector probe binding site, which is unique to a particular polymorphic target polynucleotide; and the loop encodes a reverse primer binding site, or complement to a reverse primer binding site, which is unique to a particular polymorphic target polynucleotide. Thus, in a scenario for example where three polymorphic target polynucleotides are to be queried in a single reverse transcription reaction mixture, there are three different species of reverse stem-loop primers. The first species of reverse stem-loop primer for querying the first target polynucleotide contains a 3' target-specific portion (A), a stem (B), and a loop (C). The second reverse stem-loop primer for querying the second target polynucleotide contains a 3' target-specific portion (N), a stem (O), and a loop (P). The third reverse stem-loop primer for querying the third target polynucleotide contains a 3' target-specific portion (X), a stem (Y), and a loop (Z).

FIG. 2 depicts a design for a reverse stem-loop ligation probe according to some embodiments of the present teachings. Here, the reverse stem-loop ligation probe (5) comprises a 3' target-specific portion (8), a stem (7), and a loop (5). The 3' end of the reverse stem-loop ligation probe is shown containing a 3'NH2 group, thus preventing its extension by an enzyme such as a polymerase, reverse transcriptase, etc. As used herein, the functionality imparted by the NH2 group is generally referred to as an extension blocker. The 5' end of the reverse stem-loop ligation probe is shown containing a PO4 group, thus allowing its ligation to the 3' end of a target polynucleotide. The reverse stem-loop ligation probe can also comprise a degradable nucleotide, such as uracil, which can be degraded with uracil-N-glycosylase (UNG). Of course, analogous to the design logic discussed above for a collection of three reverse stem-loop primers, so too can the three regions of a stem-loop ligation probe uniquely encode a particular target polynucleotide.

FIG. 3 depicts one workflow overview according to some embodiments of the present teachings. Here, a multiplexed reverse transcription (RT) reaction is performed on a plurality of polymorphic target polynucleotides in an RT reaction mixture. Following the multiplexed RT, the resulting reaction products can be divided into a plurality of lower plex (for example, single-plex) decoding PCR reactions such as Taq-Man 5' nuclease PCR. Focusing on the components of one of the PCRs in a microtitre plate, such a PCR can comprise a reverse primer that was encoded by the loop of a particular reverse stem-loop primer. This PCR further contains a forward primer that is unique for a particular target polynucleotide. This PCR further contains a detector probe, such as a TaqMan 5' nuclease probe, which can be encoded by the stem of the reverse stem-loop primer. Different PCRs in the microtitre plate can contain different collections of reverse primer, forward primer, and detector probe, thus allowing for the decoding of a single target polynucleotide in each of a plurality of separate PCRs.

Analogous to the work-flow logic discussed above in FIG. 3 for a collection of three reverse stem-loop primers, so too a multiplexed ligation reaction employing reverse stem-loop ligation probes can be decoded with a plurality of lower plex (for example single-plex) PCRs. Here in the context of a ligation approach, the multiplexed ligation reaction is followed by a digestion phase prior to the RT reaction. The digestion phase is employed to remove the target-specific portion of the reverse-stem loop ligation probe by attacking degradable nucleotides, thereby allowing hybridization of a reverse primer. Any number of approaches for digestion can be employed. For example, in some embodiments the stem and/or the 3' target-specific portion and/or loop of the reverse stem-loop ligation probe can contain uracil residues as the degradable nucleotides, thus allowing for digesting with uracil-N-glycosylase (UNG). As another example, in some embodiments the stem and/or 3' target-specific portion and/or loop of the reverse stem-loop ligation probe contains RNA residues as the degradable nucleotides, thus allowing for digesting with base such as NaOH.

FIG. 5 depicts one reaction according to some embodiments of the present teachings. Here, the reverse stem-loop ligation probe design discussed in FIG. 2, can be employed in a work-flow design as discussed in FIG. 4. A target polynucleotide (9) is hybridized with a reverse stem-loop ligation probe (10) containing a 3' target-specific portion (13), a stem (12), and a loop (11). (Of course, as discussed in FIG. 2, a plurality of different reverse stem-loop ligation probes can be employed to query a plurality of different target polynucleotides). Following a ligation phase (14), the target polynucleotide is ligated with the reverse stem-loop ligation probe to form a reaction product (15).

One aspect of this approach is the target polynucleotides, which can vary only slightly from one another in their sequence, can be discriminated by using correspondingly different ligation probes which themselves have slightly varying 3' target-specific portions. The discrimination is provided by the fidelity of ligase enzyme to ligate when a complete Watson-Crick complementary match exists, but to refrain from ligating when mismatches exist. This fidelity of ligation can achieve single nucleotide discrimination. Here, when mismatches exist between the nucleotides of 3' end of the target polynucleotide and the corresponding nucleotides in the 3' target-specific portion of the reverse stem-loop ligation probe, ligation of the target polynucleotide to the reverse stem-loop ligation probe fails to occur. In the absence of such ligation, subsequent PCR amplification does not occur.

Following the ligation phase (14), a digestion phase (16) can then be performed. Digestion can remove the 3' target-specific portion and the stem of the reverse stem-loop ligation probe due to the presence of degradable nucleotides, thus resulting in an elongated target polynucleotide with a liberated end (17). A hybridization reaction (18) can then be performed, where a reverse primer (19) hybridizes to the liberated end of the an elongated target polynucleotide with a liberated end (17). (Of course, in some embodiments the 5' end of this reverse primer can hybridize to the final 3'-most nucleotides of the liberated end, as well as any of a small number of nucleotides upstream from the 3'-most nucleotides). This reverse primer, as discussed in FIGS. 1 and 2, can be encoded in the loop of the reverse stem-loop ligation probe, and can be unique to a particular target polynucleotide. Thus, when the reverse primer (19) is present in one well of a microtitre plate, but not present in a different well of the microtitre plate, a decoding PCR can be performed that selectively amplifies a desired target polynucleotide from the multiplexed ligation reaction. Such a PCR (21) can comprise the reverse primer (19), a forward primer (24), and a detector probe (23), such as for example a 5' nuclease TaqMan probe. The forward primer can contain a 3' target-specific portion (24) and a 5' tail (26). The tail of the forward primer can comprise a zipcode, allowing for the detection of the resulting PCR amplicon on a microarray, as further discussed below.

In some embodiments, the reverse stem-loop ligation probe is first phosphorylated, for example with T4 polynucleotide kinase, to add phosphate to the 5' sites, and then the phosphorylated reverse stem-loop ligation probe is ligated with the 3'-end of the target polynucleotide miRNA. In some embodiments, the dT residues in the down strand of the stem are replaced with dU residues. UNG digestion can be performed to degrade the dU residues in the stem region to destabilize the stem-loop structure. In some embodiments, the UNG treatment may be omitted, and the un-ligated reverse stem-loop ligation probe dissociated from its hybridized target by heat.

To validate the ability of the ligation-based assay to discriminate different species of shRNA-derived siRNA whose only difference is at the 3'-end, we synthesized a series of RNAs to mimic the putative anti sense strands of Sh1 shRNA-derived siRNAs designed and specific assays for each RNA species. The sequences of oligos used in the assay are provided in Table 5. We used these assays to quantify each RNA species in a series of concentrations, and the results showed that these assays can efficiently and linearly quantify these RNA targets. To demonstrate the specificity of the assay in RNA quantification, we have quantified each RNA target with assays designed for individual RNA targeta. These data indicate that each particular assay can selectively quantify the desired particular RNA target. If the assay is not matched with a target, the detecting efficiency is dramatically decreased.

After demonstrating the specificity, effectiveness and linearity of the ligation-based assay in the quantitation of siRNA, we applied the assay to quantify siRNAs in cell lines transfected with the plasmid expressing Sh1 shRNA. Total RNA samples isolated from untransfected cells (negative control) and from cells transfected with plasmids expressing Sh1-shRNA were obtained. The data from these experiments were processed as copy number of each anti sense stand of siRNA derived from shiRNA in each cell by using synthetic Sh1-AS RNA as standards and based on the assumption that each cell contains about 30 pg of total RNA. By using the ligation-based assay, Sh1 shRNA-derived siRNAs are detectable in total RNA isolated from cells transfected with plasmid expressing Sh1 shRNA, but are not detectable in total RNA isolated from untransfected cells (negative control). These results indicate that siRNA is derived from expressed Sh1 shRNA. For Sh1 shRNA expression, m0 anti sense strand (with 2 dUs at the 3'-end) is the major product in vivo. Concordance between Sh1 shRNA derived-siRNA copy number and the level of target gene expression was observed in cells transfected with plasmid expressing Sh1 shRNA. There results demonstrate that the ligation-based assay can accurately detect the copy number of shRNA-derived siRNAs in transfected cells, and the ligation-based assay correlates with in vivo functional assay.

Since shRNA can be ambiguously processed by Dicer into multiple siRNA species in vivo, we hypothesize that pre-miRNA may also be processed by Dicer into multiple miRNA species in vivo. To test our hypothesis, we designed assays specific for several putative polymorphic miRNAs. Sequences of the oligos used in the assay are provided in Table 5. We detected the presence of these putative polymorphic miRNA in total RNA samples isolated from human brain tumor tissues (38N, 3H) and human brain normal tissues (A4124, 4330). The summarized results show that both human mir-137 miRNA and human mir-100 miRNA are polymorphic. The major species of human mir-137 is m2 species, which is two nucleotides less than mature mir-137 (m0) at 3' end, the major species of human mir-100 is m1 species, which is one nucleotide less than mature mir-100 (m0) at 3' end.

It will be appreciated that the ability to quantity polymorphic polynuceotides provided by the present teachings can be practiced in the context of optimizing reverse transcription and amplification reactions as known to those skilled in the art. For example, it is known that PCR may be optimized by altering times and temperatures for annealing, polymerization, and denaturing, as well as changing the buffers, salts, and other reagents in the reaction composition. Descriptions of amplification optimization can be found in, among other places, James G. Wetmur, "Nucleic Acid Hybrids, Formation and Structure," in Molecular Biology and Biotechnology, pp. 605-8, (Robert A. Meyers ed., 1995); McPherson, particularly in Chapter 4; Rapley; and Protocols & Applications Guide, rev. September/2004, Promega.

In some embodiments, the present teachings contemplate single-tube RT-PCR approaches, and discussed for example in Mohamed et al., (2004) Journal of Clinical Virology, 30:150-156.

In some embodiments, the reverse transcription products of the present teachings can be amplified in a multiplexed pre-amplifying PCR followed by a plurality of lower-plex decoding PCRs, as described for example in WO2004/051218 to Andersen and Ruff, U.S. Pat. No. 6,605,451 to Xtrana, and U.S. Non-Provisional application Ser. No. 11/090,830 to Andersen et al., and U.S. Non-Provisional application Ser. No. 11/090,468 to Lao et al., As used herein, the term "pre-amplifying" refers to a process wherein a multiplexed PCR is performed, followed by a plurality of lower-plex decoding PCRs. Typically the primers employed in the multiplexed PCR correspond to the primers employed in the plurality of lower-plex decoding PCRs.

In some embodiments, the methods of the present teachings can employ recently developed techniques that take advantage of the sensitivity, specificity, and dynamic range of quantitative real-time PCR for the quantitation micro RNAs (see for example U.S. Non-Provisional application Ser. No. 10/881,362 to Brandis et al., Ser. No. 10/944,153 to Lao et al., Ser. No. 10/947,460 to Chen et al., and Ser. No. 11/142,720 to Chen et al.,). Further illustrations of the various relationships between 3' target-specific portion, stem, and loop, and the encoding of a corresponding detector probe, can be found described for example in U.S. Non-Provisional patent application Ser. No. 10/947,460 to Chen et al., and Ser. No. 11/142,720 to Chen et al.).

In some embodiments, the identification of the amplified target polynucleotide can employ a detector probe. Such detector probes comprise refers to a molecule used in an amplification reaction, typically for quantitative or real-time PCR analysis, as well as end-point analysis. Such detector probes can be used to monitor the amplification of the target miRNA and/or control nucleic acids such as endogenous control small nucleic acids and/or synthetic internal controls. In some embodiments, detector probes present in an amplification reaction are suitable for monitoring the amount of amplicon(s) produced as a function of time. Such detector probes include, but are not limited to, the 5'-exonuclease assay (TaqMan® probes described herein (see also U.S. Pat. No. 5,538,848) various stem-loop molecular beacons (see e.g., U.S. Pat. Nos. 6,103,476 and 5,925,517 and Tyagi and Kramer, 1996, Nature Biotechnology 14:303-308), stemless or linear beacons (see, e.g., WO 99/21881), PNA Molecular Beacons™ (see, e.g., U.S. Pat. Nos. 6,355,421 and 6,593,091), linear PNA beacons (see, e.g., Kubista et al., 2001, SPIE 4264:53-58), non-FRET probes (see, e.g., U.S. Pat. No. 6,150,097), Sunrise®/Amplifluor® probes (U.S. Pat. No. 6,548,250), stem-loop and duplex Scorpion™ probes (Solinas et al., 2001, Nucleic Acids Research 29:E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155-11161. Detector probes can also comprise quenchers, including without limitation black hole quenchers (Biosearch), Iowa Black (IDT), QSY quencher (Molecular Probes), and Dabsyl and Dabcel sulfonate/carboxylate Quenchers (Epoch). Detector probes can also comprise two probes, wherein for example a fluor is on one probe, and a quencher is on the other probe, wherein hybridization of the two probes together on a target quenches the signal, or wherein hybridization on the target alters the signal signature via a change in fluorescence. Illustrative detector probes comprising two probes wherein one molecule is an L-DNA and the other molecule is a PNA can be found in U.S. Non-Provisional patent application Ser. No. 11/172,280 to Lao et al., Detector probes can also comprise sulfonate derivatives of fluorescenin dyes with SO3 instead of the carboxylate group, phosphoramidite forms of fluorescein, phosphoramidite forms of CY 5 (commercially available for example from Amersham). In some embodiments, intercalating labels are used such as ethidium bromide, SYBR® Green I (Molecular Probes), and PicoGreen® (Molecular Probes), thereby allowing visualization in real-time, or end point, of an amplification product in the absence of a detector probe. In some embodiments, real-time visualization can comprise both an intercalating detector probe and a sequence-based detector probe can be employed. In some embodiments, the detector probe is at least partially quenched when not hybridized to a complementary sequence in the amplification reaction, and is at least partially unquenched when hybridized to a complementary sequence in the amplification reaction. In some embodiments, probes can further comprise various modifications such as a minor groove binder (see for example U.S. Pat. No. 6,486,308) to further provide desirable thermodynamic characteristics. In some embodiments, detector probes can correspond to identifying portions or identifying portion complements, also referred to as zip-codes. Descriptions of identifying portions can be found in, among other places, U.S. Pat. No. 6,309,829 (referred to as "tag segment" therein); U.S. Pat. No. 6,451,525 (referred to as "tag segment" therein); U.S. Pat. No. 6,309,829 (referred to as "tag segment" therein); U.S. Pat. No. 5,981,176 (referred to as "grid oligonucleotides" therein); U.S. Pat. No. 5,935,793 (referred to as "identifier tags" therein); and PCT Publication No. WO 01/92579 (referred to as "addressable support-specific sequences" therein).

The primers and probes of the present teachings can contain conventional nucleotides, as well as any of a variety of analogs. For example, the term "nucleotide", as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR$_2$ or halogen groups, where each R is independently H, $C_1$-$C_6$ alkyl or $C_5$-$C_{14}$ aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (see, e.g., PCT published application nos. WO 98/22489, WO 98/39352, and WO 99/14226). Exemplary LNA sugar analogs within a polynucleotide include, but are not limited to, the structures:

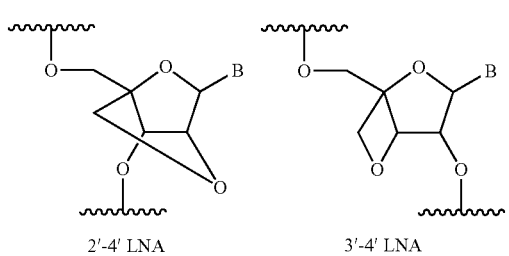

2'-4' LNA     3'-4' LNA where B is any nucleotide base.

Modifications at the 2'- or 3'-position of ribose include, but are not limited to, hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleotides include, but are not limited to, the natural D optical isomer, as well as the L optical isomer forms (see, e.g., Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleotide base is purine, e.g. A or G, the ribose sugar is attached to the $N^9$-position of the nucleotide base. When the nucleotide base is pyrimidine, e.g. C, T or U, the pentose sugar is attached to the $N^1$-position of the nucleotide base, except for pseudouridines, in which the pentose sugar is attached to the C5 position of the uracil nucleotide base (see, e.g., Kornberg and Baker, (1992) *DNA Replication*, $2^{nd}$ Ed., Freeman, San Francisco, Calif.).

One or more of the pentose carbons of a nucleotide may be substituted with a phosphate ester having the formula:

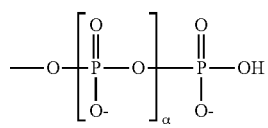

where α is an integer from 0 to 4. In certain embodiments, α is 2 and the phosphate ester is attached to the 3'- or 5'-carbon of the pentose. In certain embodiments, the nucleotides are those in which the nucleotide base is a purine, a 7-deazapurine, a pyrimidine, or an analog thereof. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group may include sulfur substitutions for the various oxygens, e.g. α-thio-nucleotide 5'-triphosphates. For a review of nucleotide chemistry, see: Shabarova, Z. and Bogdanov, A. *Advanced Organic Chemistry of Nucleic Acids*, VCH, New York, 1994.

Other terms as used herein will harbor meaning based on the context, and can be further understood in light of the understanding of one of skill in the art of molecular biology. Illustrative teachings describing the state of the art can be found, for example, in Sambrook et al., Molecular Cloning, 3rd Edition.

In some embodiments, the present teachings can also be applied where the reverse stem-loop probes comprise a library of degenerate molecules. For example, such a degenerate library can comprise a collection of reverse stem-loop ligation probes which vary in their 3' target-specific portion, and contain all possible combinations of sequence in the 3' target-specific portion. Of course, such a degenerate likely can also be employed with a reverse stem-loop primer.

In some embodiments, the present teachings can also be applied for multi-plexed microarray detection. For example, following RT, a multiplexed PCR can be performed. This PCR can comprise a fluorescently labeled primer, thus allowing the results of the multiplexed PCR to be analyzed on a microarray. Illustrative teaching of making and using labeled primers can be found, for example, in U.S. Pat. No. 6,200,748 to Smith et al., In some embodiments, the PCR can comprise a tailed primer, for example a tailed forward primer, where the tail of each forward primer contains a unique sequence (a zip-code sequence) that uniquely identifies a particular target polynucleotide. Thus, microarrays comprising complementary zip-code sequences can be used to read-out such PCR products. Illustrative teachings of detecting labeled reaction products containing zipcode sequences on complementary zipcode microarrays can be found, for example, in U.S. Pat. No. 6,852,487 to Barany et al., Thus, in some embodiments the present teachings provide a method of amplifying a target polynucleotide, the method comprising; forming a first reaction complex comprising a reverse stem-loop ligation probe hybridized to the target polynucleotide, wherein the reverse stem-loop ligation probe comprises a loop, a stem, and a 3' target-specific portion; ligating the reverse stem-loop ligation probe to the target polynucleotide to form an elongated target polynucleotide; removing the hybridized 3' target-specific portion from the elongated target polynucleotide to form an elongated target polynucleotide with a liberated end; forming a second reaction complex comprising a reverse primer hybridized to the liberated end of the elongated target polynucleotide; extending the reverse primer to form a first strand, wherein the first strand is hybridized to the elongated target polynucleotide to form a double stranded complex; and, amplifying the double stranded complex.

In some embodiments, the reverse stem-loop ligation probe comprises at least one uracil residue, wherein the removing comprises enzymatic degradation of the uracil. In some embodiments, target polynucleotide is an RNA molecule, wherein the reverse stem-loop ligation probe is a DNA molecule, and wherein the ligase is T4 DNA ligase. In some embodiments, the liberated end of the elongated target polynucleotide corresponds to the loop of the reverse stem-loop ligation probe. In some embodiments, the amplifying comprises a PCR, wherein the PCR comprises a forward primer, and wherein the forward primer comprises a target-specific portion and a 5' tail. In some embodiments, the amplifying is a real-time PCR. In some embodiments, the real-time PCR comprises a nucleic acid detector probe, wherein the nucleic acid detector probe comprises a sequence complementary to the stem of the reverse stem-loop ligation probe, or comprises a sequence complementary to the complement of the stem of the reverse stem-loop ligation probe. In some embodiments, the nucleic acid detector probe further comprises a sequence complementary to the target polynucleotide, or comprises a sequence complementary to the complement of the target polynucleotide. In some embodiments, the detector probe is a 5' nuclease cleavable probe. In some embodiments, the 3' target-specific portion of the reverse stem-loop ligation probe comprises an extension blocker. In some embodiments, the extension blocker is an amine group.

The present teachings also provide reaction compositions. The reaction compositions provided by the present teachings can be employed in the methods of the present teachings. For example, when three species of reverse stem-loop ligation probes are employed to query three different target polynucleotides, each of the three species of reverse stem-loop ligation probes can vary in their loop, stem, and 3' target-specific portion. However, in some embodiments, the methods of the present teachings can be employed with a collection of reverse stem-loop ligation probes which vary only in their 3' target-specific portions, and contain the same, or closely similar, stems and/or loops. Such approaches can allow a single universal reverse primer to query a variety of different elongated target polynucleotides. The use of such universal reverse primers is discussed, for example, in Chen et al., U.S. Non-Provisional application Ser. Nos. 10/947,460, and 11/142,720 to Chen et al.

In some embodiments the present teachings provide a reaction composition comprising at least three species of reverse stem-loop ligation probes, wherein the at least three species of reverse stem-loop ligation probes vary from each other in the sequence of the 3' target-specific portion, wherein the at least three species of reverse stem-loop ligation probes vary from each other in the sequence of their stem, and wherein the at least three species of reverse stem-loop ligation probes vary from each other in the sequence of their loop. In some embodiments, the at least three species of reverse stem-loop ligation probes each comprise an extension blocker, a degradable nucleotide, or both an extension blocker and a degradable nucleotide. In some embodiments, the 3' target-specific portion comprises the extension blocker, and the stem comprises the degradable nucleotide. In some embodiments, the 3' target-specific portion of each of the at least three species of reverse stem-loop ligation probes is complementary to an ShRNA-derived siRNA. In some embodiments, the reaction composition can comprise at least four reverse stem-loop ligation probes, at least five reverse stem-loop ligation probes, at least ten reverse stem-loop ligation probes, at least fifty reverse stem-loop ligation probes, at least one-hundred reverse stem-loop ligation probes, at least two hundred reverse stem-loop ligation probes, between four and one-hundred reverse stem-loop ligation probes, between four and two-hundred reverse stem-loop ligation probes, or between four and three-hundred reverse stem-loop ligation probes.

In some embodiments, the present teachings provide a reaction composition comprising at least three species of reverse stem-loop primers, wherein the at least three species of reverse stem-loop primers vary from each other in the sequence of the 3' target-specific portion, wherein the at least three species of reverse stem-loop primers vary from each other in the sequence of their stem, and wherein the at least three species of reverse stem-loop primers vary from each other in the sequence of their loop. In some embodiments, the at least three species of reverse stem-loop primers each comprise a degradable nucleotide. In some embodiments, the stem comprises the degradable nucleotide. In some embodiments, the 3' target-specific portion of each of the at least three species of reverse stem-loop ligation probes is complementary to an ShRNA-derived siRNA.

Certain Exemplary Kits

The instant teachings also provide kits designed to expedite performing certain of the disclosed methods. Kits may serve to expedite the performance of certain disclosed methods by assembling two or more components required for carrying out the methods. In certain embodiments, kits contain components in pre-measured unit amounts to minimize the need for measurements by end-users. In some embodiments, kits include instructions for performing one or more of the disclosed methods. Preferably, the kit components are optimized to operate in conjunction with one another.

Thus, in some embodiments the present teachings provide a kit for amplifying at least three target polynucleotides, the kit comprising at least three species of reverse stem-loop ligation probes, wherein the at least three species of reverse stem-loop ligation probes vary from each other in the sequence of the 3' target-specific portion, wherein the at least three species of reverse stem-loop ligation probes vary from each other in the sequence of their stem, and wherein the at least three species of reverse stem-loop ligation probes vary from each other in the sequence of their loop. In some embodiments, the at least three species of reverse stem-loop ligation probes comprise an extension blocker, a degradable nucleotide, or both an extension blocker and a degradable nucleotide. In some embodiments, the kit further comprises a reverse transcriptase. In some embodiments, the kit further comprises a polymerase. In some embodiments the kit further comprises a reverse primer, a forward primer, and a detector probe.

In some embodiments, the present teachings provide a kit for amplifying at least two different target polynucleotides in a family of target polynucleotides, wherein the at least two different target polynucleotides in the family of target polynucleotides vary in no more than two nucleotides in the last nucleotides at their 3' end regions, the kit comprising at least two species of reverse stem-loop ligation probes, wherein the two species of reverse stem-loop ligation probes vary from each other in their 3' target-specific portions. In some embodiments, the at least two species of reverse stem-loop ligation probes vary from each other in the sequence of the 3' target-specific portion, wherein the at least two species of reverse stem-loop ligation probes vary from each other in the sequence of their stem, and wherein the at least two species of reverse stem-loop ligation probes vary from each other in the sequence of their loop. In some embodiments, the at least two species of reverse stem-loop ligation probes comprise an extension blocker, a degradable nucleotide, or both an extension blocker and a degradable nucleotide. In some embodiments the kit further comprises a reverse transcriptase. In some embodiments the kit further comprises a polymerase. In some embodiments, the kit further comprises a reverse primer, a forward primer, and a detector probe. In some embodiments the family of target polynucleotides are ShRNA-derived siRNAs.

EXAMPLES

TABLE 1

| 1. Ligation/kinase | | | |
|---|---|---|---|
| Items | Stock | Reaction | Volume (uL) |
| RNA sample | 3x (12 ng/ul) | 1x (4 ng/ul) | 2.50 |
| reverse stem-loop ligation probe | 150 nm | 50 nm | 2.50 |
| Ligation Reaction Mix | | | |
| T4 polynucleotide kinase (10 U/uL, NEB, M0201L) | 10 U/uL | 0.5 U/uL | 0.375 |
| T4 DNA ligase (2000 U/uL, NEB, M0202M) | 2000 U/uL | 50 U/uL | 0.188 |
| T4 DNA Ligase buffer (NEB, B02025) | 10 x | 1 x | 0.750 |
| AB RNase Inhibitor (P/N: N8080119) | 20 U/uL | 0.5 U/uL | 0.188 |
| H2O | | | 1.000 |
| Total | | | 7.50 |

Incubate at 16° C./30 min, 37° C./60 min, 4° C. on hold.

TABLE 2

2. Digestion

| Items | Stock (u/ul) | Mixture | Reaction | Volume (ul) |
|---|---|---|---|---|
| UNG (NEB, M0280L) | 2 | 0.4 | 0.1 | 0.1 |
| AB RNase Inhibitor (P/N: N8080119) | 20 | 0.5 | | 0.125 |
| T4 DNA Ligase buffer (NEB, B02025) | 10 | 1 | | 0.25 |
| H20 | | | | 2.025 |
| Total | | | | 2.50 |

Add 2.5 ul of UNG mix to 7.5 ul of ligation mix, 37° C./60 min, 4° C. on hold.

TABLE 3

3. RT

| Items | Stock | | [1x] | | Volume (uL) |
|---|---|---|---|---|---|
| RT primer | 5 | um | 1 | um | 3.00 |
| Ligation-digestion Product | 3 | x | 1 | x | 5.00 |
| RT Enzyme Mix | | | | | |
| dNTPs with dTTP (P/N: 8080261) | 25 | mM each | 0.25 | mM each | 0.150 |
| MultiScribe Reverse Transcriptase (P/N: 4319983) | 50 | x | 3.33 | x | 1.000 |

TABLE 3-continued

3. RT

| Items | Stock | | [1x] | | Volume (uL) |
|---|---|---|---|---|---|
| 10X RT Buffer (P/N: 4319981) | 10 | x | 1 | x | 1.500 |
| AB RNase Inhibitor (P/N: N8080119) | 20 | U/uL | 0.25 | U/uL | 0.188 |
| Nuclease-free dH2O | | | | | 4.163 |
| Total | | | | | 15.00 |

Incubate at 45° C. for 45 min, 85° C./5 min, 4° C. on hold

TABLE 4

4. PCR

| Items | Stock | | [1x] | | Volume (uL) |
|---|---|---|---|---|---|
| RT products | 15 | x | 1 | x | 2.00 |
| 2X TaqMan Master Mix, No UNG (P/N: 4324018) | 2 | x | 1 | x | 15.00 |
| 10X Ppi mixture | 10 | x | 1 | x | 3.00 |
| Nuclease-free dH2O | | | | | 10.00 |
| Total | | | | | 30.00 |

Transfer 10 ul to each well in 384-well plate, duplicate. Cycling at 95° C./10 min, [95° C./15 sec, 60° C./60 sec]×40 cycles. Use FAM as reporter, at 7900HT.

TABLE 5

| | ID | Sequence |
|---|---|---|
| Reverse stem-loop ligation probe | Sh1AS-m2_L6 | GACGCAAAGGAAGAGTGGGAGCGTGC(dU)(dU)C (dU)(dU)CC(dU)(dU)(dU)GCGTCGCGGAG(NH2) [SEQ ID NO: 1] |
| | Sh1AS-m1_L6 | CCAGGCAAGAAGCCGCCAACCTCTCG(dU)(dU)C C(dU)(dU)C(dU)(dU)GCCTGGAGCGGA(NH2) [SEQ ID NO: 2] |
| | Sh1AS-m0_L6 | GAGGCAAGGAAGTGGCGGTAGCTGGC(dU)(dU)A C(dU)(dU)CC(dU)(dU)GCCTCAAGCGG(NH2) [SEQ ID NO: 3] |
| | Sh1AS-p1_L6 | GACAACGAGACACCTGCGAGTGACCC(dU)(dU)G (dU)G(dU)C(dU)CG(dU)TGTCAAAGCG(NH2) [SEQ ID NO: 4] |
| | Sh1AS-p2_L6 | GACGGCAAGGAGGTCCGCACTCTCCG(dU)(dU)C C(dU)CC(dU)(dU)GCCGTCAAAAGC(NH2) [SEQ ID NO: 5] |
| Forward primer | Sh1AS-m2_F | CGCGCTCTTCGTCGCTG [SEQ ID NO: 6] |
| | Sh1AS-m1_F | CGCGCTCTTCGTCGCTG [SEQ ID NO: 7] |
| | Sh1AS-m0_F | CGCGCTCTTCGTCGCTG [SEQ ID NO: 8] |
| | Sh1AS-p1_F | CGCGCTCTTCGTCGCTG [SEQ ID NO: 9] |
| | Sh1AS-p2_F | CGCGCTCTTCGTCGCTG [SEQ ID NO: 10] |
| Reverse PCR primer | Sh1AS-m2_LR | GCACGCTCCCACTCTTC [SEQ ID NO: 11] |
| | Sh1AS-m1_LR | GAGAGGTTGGCGGCT [SEQ ID NO: 12] |
| | Sh1AS-m0_LR | CAGCTACCGCCACTTC [SEQ ID NO: 13] |
| | Sh1AS-p1_LR | GGGTCACTCGCAGGTG [SEQ ID NO: 14] |
| | Sh1AS-p2_LR | GAGAGTGCGGACCTCC [SEQ ID NO: 15] |
| TagMan probe | Sh1AS-m2_T | (6-FAM)CTTTGCGTCGCGGAGA(MGB) [SEQ ID NO: 16] |
| | Sh1AS-m1_T | (6-FAM)CTTGCCTGGAGCGGAGA(MGB) [SEQ ID NO: 17] |
| | Sh1AS-m0_T | (6-FAM)TTGCCTCAAGCGGAGAC(MGB) [SEQ ID NO: 18] |
| | Sh1AS-p1_T | (6-FAM)TCGTTGTCAAAGCGGAG(MGB) [SEQ ID NO: 19] |
| | Sh1AS-p2_T | (6-FAM)TGCCGTCAAAAGC(MGB) [SEQ ID NO: 20] |
| RT primer | Sh1AS-m2_RT | GCACGCTCCCACTCTTC [SEQ ID NO: 21] |
| | Sh1AS-m1_RT | GAGAGGTTGGCGGCTT [SEQ ID NO: 22] |
| | Sh1AS-m0_RT | GCCAGCTACCGCCACT [SEQ ID NO: 23] |

TABLE 5-continued

| | ID | Sequence |
|---|---|---|
| | Sh1AS-p1_RT | GGGTCACTCGCAGGTGT [SEQ ID NO: 24] |
| | Sh1AS-p2_RT | CGGAGAGTGCGGACCTC [SEQ ID NO: 25] |
| Reverse stem-loop ligation probe | has-mir-137-m2_L5 | GCACTGATGGCAGACCGATCCTTGGTTGCA(dU)(dU)(dU)C(dU)GCCA(dU)CAG(dU)GCACGCG(NH2) [SEQ ID NO: 26] |
| | has-mir-137-m1_L5 | TTACCGACGTCAGAGCCCAGTCTAATCGCA(dU)(dU)(dU)C(dU)GACG(dU)CGG(dU)AATACGC(NH2) [SEQ ID NO: 27] |
| | has-mir-137-m0_L5 | GGACCCATGTCAGACCTCACACACTACCTG(dU)(dU)(dU)C(dU)GACA(dU)GGG(dU)CCCTACG(NH2) [SEQ ID NO: 28] |
| | has-mir-137-p1_L5 | GGACTGATCGCAGAGAGCAAGCAGTTCACT(dU)(dU)(dU)C(dU)GCGA(dU)CAG(dU)CCACTAC(NH2) [SEQ ID NO: 29] |
| | has-mir-137-p2_L5 | GCAGCGATCTCAGAGGCTCGTGATCATGAA(dU)(dU)(dU)C(dU)GAGA(dU)CGC(dU)GCGACTA(NH2) [SEQ ID NO: 30] |
| | has-mir-100-m2_L5 | GGACTGATGGCAGACGGATCGTTGGTTGCT(dU)(dU)(dU)C(dU)GCCA(dU)CAG(dU)CCCAAGT(NH2) [SEQ ID NO: 31] |
| | has-mir-100-m1_L5 | TTACGGACGTCAGAGCCCAGTCTAATCGCA(dU)(dU)(dU)C(dU)GACG(dU)CCG(dU)AAACAAG(NH2) [SEQ ID NO: 32] |
| | has-mir-100_m0_L5 | TTAGGCAGGTCAGACATCGTACCCTACCAG(dU)(dU)(dU)C(dU)GACC(dU)GCC(dU)AACACAA(NH2) [SEQ ID NO: 33] |
| | has-mir-100-p1_L5 | GGACTGATCGCAGAGAGCAAGCAGTACTCT(dU)(dU)(dU)C(dU)GCGA(dU)CAG(dU)CCCCACA(NH2) [SEQ ID NO: 34] |
| | has-mir-100-p2_L5 | GCAGTGACCTCAGAGGGAGCTGATCATGAA(dU)(dU)(dU)C(dU)GAGG(dU)CAC(dU)GCACCAC(NH2) [SEQ ID NO: 35] |
| Forward primer | has-mir-137-m2_F | GCTCCGCTATTGCTTAAGAATACGC [SEQ ID NO: 36] |
| | has-mir-137-m1_F | GCTCCGCTATTGCTTAAGAATACGC [SEQ ID NO: 37] |
| | has-mir-137-m0_F | GCTCCGCTATTGCTTAAGAATACGC [SEQ ID NO: 38] |
| | has-mir-137-p1_F | GCTCCGCTATTGCTTAAGAATACGC [SEQ ID NO: 39] |
| | has-mir-137-p2_F | GCTCCGCTATTGCTTAAGAATACGC [SEQ ID NO: 40] |
| | has-mir-100-m2_F | GCCGAACCCGTAGATCCGAA [SEQ ID NO: 41] |
| | has-mir-100-m1_F | GCCGAACCCGTAGATCCGAA [SEQ ID NO: 42] |
| | has-mir-100_m0_F | GCCGAACCCGTAGATCCGAA [SEQ ID NO: 43] |
| | has-mir-100-p1_F | GCCGAACCCGTAGATCCGAA [SEQ ID NO: 44] |
| | has-mir-100-p2_F | GCCGAACCCGTAGATCCGAA [SEQ ID NO: 45] |
| TaqMan probe | has-mir-137-m2_T | (6-FAM)TGCCATCAGTGCACG(MGB) [SEQ ID NO: 46] |
| | has-mir-137-m1_T | (6-FAM)TGACGTCGGTAATACG(MGB) [SEQ ID NO: 47] |
| | has-mir-137-m0_T | (6-FAM)TGACATGGGTCCCTACG(MGB) [SEQ ID NO: 48] |
| | has-mir-137-p1_T | (6-FAM)TGCGATCAGTCCACTAC(MGB) [SEQ ID NO: 49] |
| | has-mir-137-p2_T | (6-FAM)TGAGATCGCTGCGACTA(MGB) [SEQ ID NO: 50] |
| | has-mir-100-m2_T | (6-FAM)TGCCATCAGTCCCAAGT(MGB) [SEQ ID NO: 51] |
| | has-mir-100-m1_T | (6-FAM)TGACGTCCGTAAACAA(MGB) [SEQ ID NO: 52] |
| | has-mir-100_m0_T | (6-FAM)TGACCTGCCTAACACAA(MGB) [SEQ ID NO: 53] |
| | has-mir-100-p1_T | (6-FAM)TGCGATCAGTCCCCACA(MGB) [SEQ ID NO: 54] |
| | has-mir-100-p2_T | (6-FAM)TGAGGTCACTGCACCAC(MGB) [SEQ ID NO: 55] |
| RT primer/PCR reverse primer | has-mir-137-m2_R | TGCAACCAAGGATCGGTC [SEQ ID NO: 56] |
| | has-mir-137-m1_R | TGCGATTAGACTGGGCTC [SEQ ID NO: 57] |
| | has-mir-137-m0_R | CAGGTAGTGTGTGAGGTC [SEQ ID NO: 58] |
| | has-mir-137-p1_R | AGTGAACTGCTTGCTCTC [SEQ ID NO: 59] |
| | has-mir-137-p2_R | TTCATGATCACGAGCCTC [SEQ ID NO: 60] |
| | has-mir-100-m2_R | AGCAACCAACGATCCGTC [SEQ ID NO: 61] |
| | has-mir-100-m1_R | TGCGATTAGACTGGGCTC [SEQ ID NO: 62] |

TABLE 5-continued

| ID | Sequence |
|---|---|
| has-mir-100_m0_R | CTGGTAGGGTACGATGTC [SEQ ID NO: 63] |
| has-mir-100-p1_R | AGAGTACTGCTTGCTCTC [SEQ ID NO: 64] |
| has-mir-100-p2_R | TTCATGATCAGCTCCCTC [SEQ ID NO: 65] |

Although the disclosed teachings have been described with reference to various applications, methods, and kits, it will be appreciated that various changes and modifications may be made without departing from the teachings herein. The foregoing examples are provided to better illustrate the present teachings and are not intended to limit the scope of the teachings herein. Certain aspects of the present teachings may be further understood in light of the following claims.

We claim:

1. A kit for amplifying at least three target polynucleotides, the kit comprising:
   at least three species of reverse stem-loop ligation probes, wherein the at least three species of reverse stem-loop ligation probes vary from each other in the sequence of the 3' target-specific portion, wherein the at least three species of reverse stem-loop ligation probes vary from each other in the sequence of their stem, wherein the at least three species of reverse stem-loop ligation probes vary from each other in the sequence of their loop, wherein the at least three species of reverse stem-loop ligation probes comprise an extension blocker, and wherein the at least three species of reverse stem-loop ligation probes comprise at least one degradable nucleotide within their 3' target-specific portion, stem, or loop; and
   an agent capable of digesting the degradable nucleotide within the probes.

2. The kit according to claim 1, further comprising a reverse transcriptase.

3. The kit according to claim 1, further comprising a polymerase.

4. The kit according to claim 1, further comprising a reverse primer, a forward primer, and a detector probe.

5. The kit according to claim 1, wherein the degradable nucleotide is an RNA residue.

6. The kit according to claim 1, wherein the degradable nucleotide is uracil.

7. The kit according to claim 6, wherein the agent is a uracil-N-glycosylase.

8. A kit for amplifying at least two different target polynucleotides in a family of target polynucleotides, wherein the at least two different target polynucleotides in the family of target polynucleotides vary in no more than two nucleotides in the last three nucleotides at their 3' end regions, the kit comprising:
   at least two species of reverse stem-loop ligation probes, wherein the at least two species of reverse stem-loop ligation probes vary from each other in their 3' target-specific portions, in the sequence of their stem, and in the sequence of their loop, wherein the at least two species of reverse stem-loop ligation probes comprise an extension blocker, and wherein the at least two species of reverse stem-loop ligation probes comprise at least one degradable nucleotide within their 3' target-specific portion, stem, or loop; and
   an agent capable of digesting the degradable nucleotide within the probes.

9. The kit according to claim 8, further comprising a reverse transcriptase.

10. The kit according to claim 8, further comprising a polymerase.

11. The kit according to claim 8, further comprising a reverse primer, a forward primer, and a detector probe.

12. The kit according to claim 8, wherein the family of target polynucleotides are ShRNA-derived siRNAs.

13. A reaction composition comprising:
    at least three species of reverse stem-loop ligation probes, wherein the at least three species of reverse stem-loop ligation probes vary from each other in the sequence of the 3' target-specific portion, wherein the at least three species of reverse stem-loop ligation probes vary from each other in the sequence of their stem, wherein the at least three species reverse stem-loop ligation probes vary from each other in the sequence of their loop, wherein the at least three species of reverse stem-loop ligation probes comprise an extension blocker, and wherein the at least three species of reverse stem-loop ligation probes comprise at least one degradable nucleotide within their 3' target-specific portion, stem or loop; and
    an agent capable of digesting the degradable nucleotide within the probes.

14. The reaction composition according to claim 13, wherein the 3' target-specific portion comprises the extension blocker, and wherein the stem comprises the degradable nucleotide.

15. The reaction composition according to claim 13, wherein the 3' target-specific portion of each of the at least three species of reverse stem-loop ligation probes is complementary to an ShRNA-derived siRNA.

16. The reaction composition according to claim 13, wherein the degradable nucleotide is an RNA residue.

17. The reaction composition according to claim 13, wherein the degradable nucleotide is uracil.

18. The reaction composition according to claim 17, wherein the agent is a uracil-N-glycosylase.

* * * * *